United States Patent [19]

Salerno et al.

[11] Patent Number: 5,336,170
[45] Date of Patent: Aug. 9, 1994

[54] SURGICAL SITE VISUALIZATION WAND

[75] Inventors: Tomas A. Salerno, Toronto, Canada; Douglas G. Fox, Holladay, Utah

[73] Assignee: Research Medical, Inc., Midvale, Utah

[21] Appl. No.: 921,553

[22] Filed: Jul. 29, 1992

[51] Int. Cl.⁵ ............................................. A61M 5/00
[52] U.S. Cl. ................................ 604/24; 604/264; 604/902; 606/190; 15/322; 239/416.4; 239/424
[58] Field of Search .................. 604/23, 24, 26, 33–35, 604/250, 264, 275, 313–316, 902; 128/863; 606/190; 15/320–322, 405; 239/597, 413, 416.4, 423, 424

[56] References Cited

U.S. PATENT DOCUMENTS

| | | | |
|---|---|---|---|
| 593,013 | 11/1897 | Fisher | 239/423 |
| 2,029,141 | 1/1936 | Warner | 15/322 |
| 2,052,622 | 9/1936 | Hale | 239/416.4 |
| 2,172,193 | 9/1939 | Downs | 239/416.4 |
| 2,757,667 | 4/1952 | Bronk . | |
| 2,984,452 | 5/1961 | Hooper . | |
| 3,254,646 | 6/1966 | Staunt et al. . | |
| 3,374,789 | 3/1968 | Maurer | 604/24 |
| 3,481,338 | 12/1969 | Sobel et al. | 606/190 |
| 3,698,088 | 10/1972 | Austin, Jr. . | |
| 4,108,178 | 8/1978 | Betush . | |
| 4,350,158 | 9/1982 | Hudson . | |
| 4,378,804 | 4/1983 | Cortese, Jr. | 604/315 |
| 4,551,131 | 11/1985 | Miles et al. | 604/35 |
| 4,569,482 | 2/1986 | Hiruma et al. | 239/424 |
| 4,673,161 | 6/1987 | Flynn et al. | 604/34 |
| 4,709,697 | 12/1987 | Muller | 606/190 |
| 4,735,606 | 4/1988 | Davison | 604/35 |
| 4,892,526 | 1/1989 | Reese . | |
| 4,941,872 | 7/1990 | Felix et al. | 604/902 |
| 5,167,220 | 12/1992 | Brown . | |
| 5,203,769 | 4/1993 | Clement et al. | 604/902 |
| 5,242,387 | 9/1993 | Loughlin . | |

FOREIGN PATENT DOCUMENTS

| | | | |
|---|---|---|---|
| 137412 | 9/1952 | Denmark | 604/225 |
| 35067 | 12/1929 | France . | |
| 1039005 | 10/1953 | France . | |
| 8911885 | 12/1989 | PCT Int'l Appl. | 604/313 |
| 334130 | 12/1958 | Switzerland . | |
| 6084 | of 1909 | United Kingdom | 604/23 |

*Primary Examiner*—Ralph Lewis
*Attorney, Agent, or Firm*—Trask, Britt & Rossa

[57] ABSTRACT

A disposable visualization wand for removal of bodily fluids from a graft, wound or other target site on a patient. The wand includes a barrel having a fan tip outlet, and a inlet end secured to a filter for removing contaminants from a gas stream feed for the wand. Also included is a liquid feed into the wand, for moisturizing the gas stream and preventing dehydration of the patient's tissue at the target site.

7 Claims, 2 Drawing Sheets

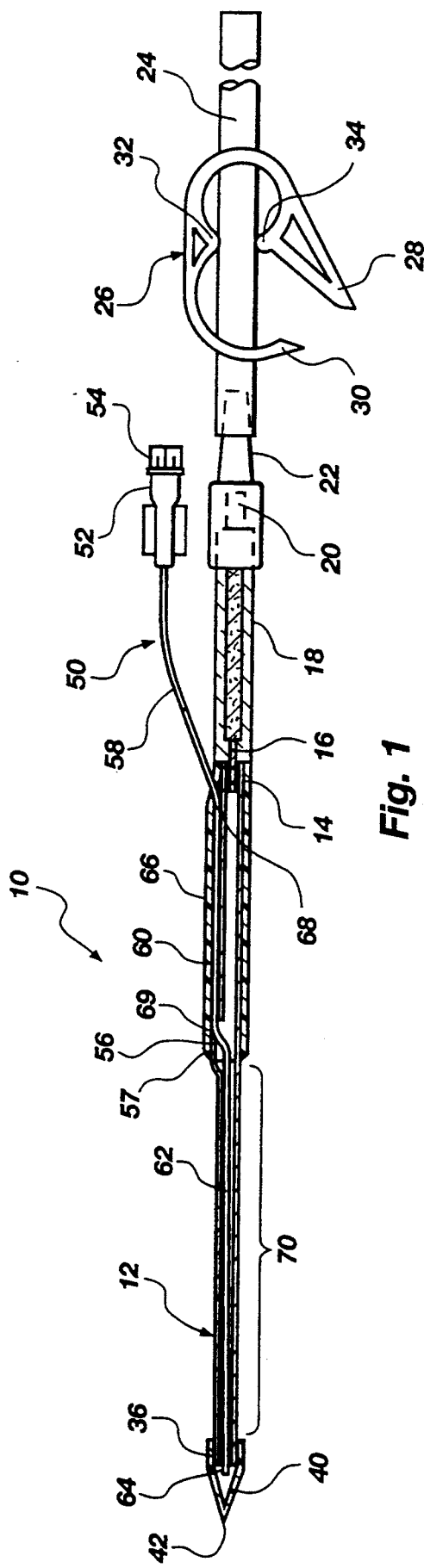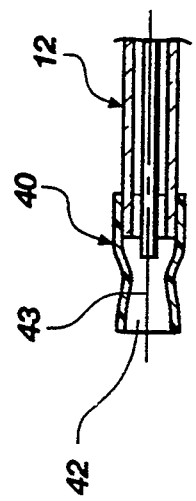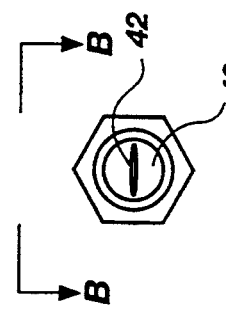
Fig. 1
Fig. 1A
Fig. 1B

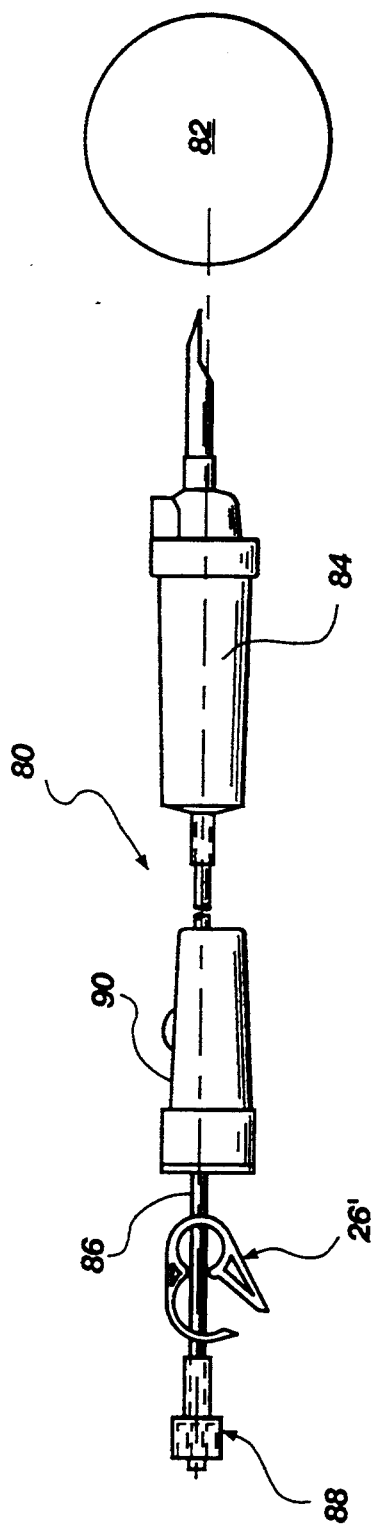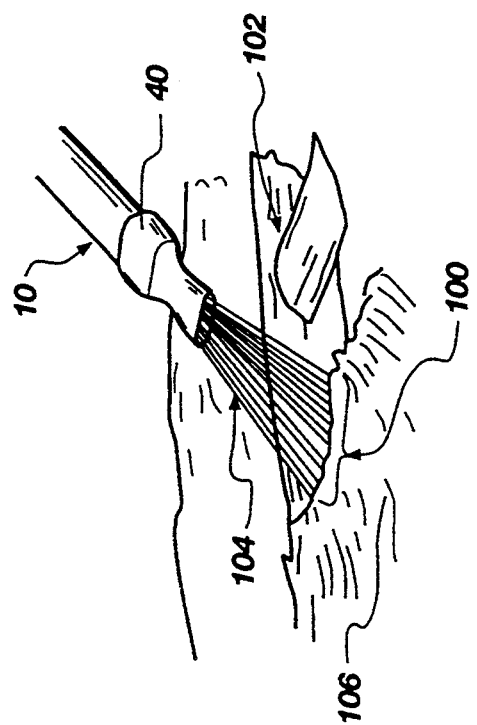

SURGICAL SITE VISUALIZATION WAND

BACKGROUND OF THE INVENTION

1. Field of the Invention

The present invention relates generally to surgical procedures, more specifically to an apparatus for the removal of excess bodily fluids from the immediate surgical field during surgery, and most specifically to an apparatus for the removal of blood from the graft area during anastomosis procedures.

2. State of the Art

During surgical procedures, and particularly many delicate present-day surgical procedures requiring and unobscured view of an extremely small surgical field within the body cavity of a patient, blood leakage becomes a major visual obstruction. Suction wands, which remove fluids from the body cavity of a patient, have been well known for decades. However, suction wands cannot be placed immediately proximate the area in which the surgeon is working without obstructing his instruments, his hands and/or his vision. Moreover, suction applied in the area of a graft or other incision site being sutured may distort the tissues or even cause damage due to stresses caused by the suction on the tissue-suture interface.

In order to address the above problem, some surgical practitioners have begun connecting a conventional suction wand to a compressed air supply in the operating theatre, and blowing blood away from the wound site using this makeshift apparatus. Several problems are attendant to this approach, however. First, the air supply may be septic, and use thereof may actually introduce bacterial and viral microorganisms into the wound site, to the detriment of the patient. Second, a surgical wand does not direct the air flow for effective removal of the blood from the wound site, and the impact of the point-focused high pressure air discharge from the wand may cause trauma. Third, use of compressed air in such a manner quickly dries the tissues surrounding the wound site, requiring periodic irrigation to prevent tissue dehydration necrosis, slowing the surgical procedure. Finally, the uncontained and undirected flow of air from a suction wand may result in spattering of blood on the surgical team, an extremely hazardous consequence in view of the possibility of HIV exposure from the patient's bodily fluids.

Numerous patents disclose irrigation apparatus of the prior art. For example, U.S. Pat. No. 4,350,158 discloses a pulsating type irrigation spray nozzle, the liquid being drawn by pressure applied to the exterior of a collapsible reservoir. U.S. Pat. No. 4,892,526 discloses an unpressurized manual pump and spray nozzle combination for drawing irrigation fluid from a reservoir and dispensing it on the tissue to be irrigated. The '526 patent is also noteworthy in that it teaches the prior art use of pressurized systems for dispensing a pressurized jet of air and/or fluid onto the tissue, and confirms that such a practice using devices of the prior art may result in over-irrigation of the exposed tissue, as well as tissue damage due to fluid impact.

Dental practitioners have employed syringes for supplying air, water or air and water to the mouth of the patient via the use of valves and a manifold associated with the syringe. See, for example, U.S. Pat. Nos. 2,757,667; 2,984,452; 3,254,646; and 4,108,178. The '667 and '452 patents also disclose the medical and female hygienic utility of such syringes. Such a syringe, which also includes the ability to provide liquid medication, alone or in combination with air, is disclosed in U.S. Pat. No. 3,698,088.

Also known in the prior art are devices for the disposition of medication-laden warm air on the patient (Swiss Patent No. 334,130); the warming of air passing through a dental syringe (French Patent No. 1,039,005) and for the disposition of electrically-warmed air onto a body surface through a cone-shaped outlet (French Patent of Addition No. 35,067). All of the prior art devices and methodologies possess one or more major deficiencies with respect to the problem of maintaining the surgical field free from bodily fluid obstruction without deleterious effect to the patient's tissue.

SUMMARY OF THE INVENTION

The present invention comprises an apparatus for the sweeping of bodily tissues with a directed gas stream for enhanced visibility and accessibility or, stated alternatively, a surgical site visualization wand.

The present invention includes, in its most basic form, a fluid delivery conduit having a fan-shaped outlet or tip defining a laterally elongated, or slit-shaped orifice, for the delivery of a substantially planar, pressurized gas stream to a specific location, such as a graft site during an anastomosis procedure. For purposes of simplicity, the area of desired delivery of the gas stream will hereinafter be referred to as the "target site". The planar gas stream permits the brushing or sweeping of excess bodily fluids, such as blood, away from the target site without tissue trauma and in a directed manner toward a removal device, such as a suction wand.

It is also desirable that the conduit have associated with the inlet thereof a fine filter for the removal of bacterial and vital microorganisms which might prove deleterious to the patient if driven into the patient's tissue at the target site.

A further desirable feature of the invention is the addition of a humidification or moisturization conduit for the selective introduction of a sterile liquid, such as saline solution, with or without added medication, in the form of a mist carried by and intermixed with the gas stream to the target site.

It is preferred that the present invention be of inexpensive construction, so as to render it cost effective for a single use with subsequent disposal.

BRIEF DESCRIPTION OF THE DRAWINGS

FIG. 1 depicts the disposable surgical site visualization wand of the present invention in a side sectional elevation;

FIG. 1A is a front elevation of the tip of the disposable surgical site visualization wand of the present invention taken across line A—A of FIG. 1;

FIG. 1B is a top sectional elevation of the tip and forward end of the disposable surgical site visualization wand of the present invention, taken across line B—B of FIG. 1A.

FIG. 2 depicts the components of a fluid connection line suitable for use with the disposable surgical site visualization wand of the present invention; and FIG. 3 is a perspective view of the tip and forward end of the disposable surgical site visualization wand of the present invention, depicting the flow of gas and/or mist from the tip onto a target site.

DETAILED DESCRIPTION OF THE PREFERRED EMBODIMENT

Referring to FIGS. 1 and 2 of the drawings, disposable surgical site visualization wand 10 of the present invention includes, in its preferred embodiment, barrel 12 comprised of a section of tubing and having its inlet end 14 connected to the outlet end 16 of gas filter 18, which is preferably a commercially available 0.22 micron filter. The inlet end 20 of filter 18 is connected via adapter 22 to a length of flexible delivery tubing 24 (preferably ⅜" O.D.) leading to a source (not shown) of pressurized gas, such as air, carbon dioxide or nitrogen, all of such gas sources being normally available in an operation theatre. The type of gas or the nature of the source thereof being immaterial to the present invention, no further description thereof will be made. Flexible plastic pinch clamp 26, of a type known in the art, is disposed about delivery tubing 24 for the selective partial or total occlusion, by pinching, of delivery tubing 24 to stop the gas stream without altering the gas flow adjustment. Engagement of leg 28 with the inner surface of leg 30 will lock clamp 26 in a closed position, wherein delivery tubing 24 will be totally collapsed between pinch bars 32 and 34 of the clamp 26.

The outlet end 36 of barrel 12 of wand 10 is secured to a tip or nozzle 40, the outlet of which is fan-shaped and defines a laterally elongated or slit-shaped orifice 42. Tip or nozzle 40 is preferably flexible, soft, and rounded on all of its exterior surfaces, to minimize any damage to the tissue of the target site from inadvertent contact. A suitable tip material is polyvinyl chloride (PVC), and the tip may be formed by dipping a mold in liquid PVC. Other methods and materials known in the art may also be utilized. It is preferable that nozzle or tip 40 include a tapered down portion 43, the purpose of which will be explained hereafter.

Liquid delivery conduit 50 extends from an adaptor 52 having a vented male luer lock cap 54 secured thereto, into barrel 12 through an aperture 56 formed through the wall thereof. In the preferred embodiment, liquid delivery conduit 50 comprises a series of progressively smaller portions, commencing with a 0.110" O.D. portion 58, leading to a 0.060" O.D. portion 60 which extends through aperture 56 into the interior of tubing section 12, and terminating in 0.038" portion 62, the outlet 64 of which is disposed within tip 40 proximate or within tapered down portion 43. The foregoing arrangement is by way of example only and alternative structures may be employed. As gas moves through tip 40, the neck or constriction 43 will accelerate the flow thereof, causing increased turbulence to facilitate the atomization of liquid emanating from outlet 64.

A sleeve 66 of flexible tubing, such as silicone tubing, envelops barrel 12 from a location proximate the inlet end toward the outlet thereof, extending past aperture 56 and encompassing portion 60 of liquid delivery conduit 50, which extends into the right-hand side of sleeve 66 through slot 68. Sleeve 66 maintains portion 60 of conduit 50 against barrel 12, and provides a larger, more comfortable and more easily manipulable gripping surface for the use of wand 10. It is preferred that a suitable adhesive be employed to seal in area 69 between the exterior of portion 60 and the walls of aperture 56 to prevent backflow of gas from the interior of wand 10. It is also preferred that aperture 56 be located at the periphery of dimple 57 in barrel 12, to facilitate passage of portion 60 therethrough without buckling or kinking.

Referring again to barrel 12, its preferred construction is of a flexible elastomer having a malleable wire embedded in the wall thereof. The wire may be disposed along the axis of the tubing, or wound in a helix within the tubing wall, for the purpose of providing a flexible distal end 70 to barrel 12 by which the tip 40 of wand 10 may be oriented at any suitable angle to the target site, and to accommodate the handling preferences of the user. Moreover, the wire reinforcement facilitates the permanent deformation of barrel 12 into dimple 57.

The fluid connection assembly 80 of FIG. 2 provides a suitable, sterile liquid feed such as saline solution (with or without added medication) from a source 82 through an I.V. spike as known in the art (not shown), drip chamber 84 and tubing 86 into male luer connector 88 which is removably engagable with male luer lock cap 54. Disposed about tubing 86 is a pinch clamp 26' of the type previously described, but sized for the smaller diameter (0.140" O.D.) tubing 86. Also disposed about tubing 86 is a suitable thumb-operated clamp 90, such as a cam-actuated roller clamp, for ease of selective occlusion and partial occlusion of tubing 86 for starting, stopping and regulating liquid flow into wand 10 during a surgical procedure. Drip chamber 84 is generally employed in conjunction with an elevated I.V. bag with pressure cuff for primary control of the maximum liquid feed rate into wand 10, further regulation being provided by clamp 90. Of course, an unpressurized liquid source may also be employed, using gravity feed for the liquid component of the fluid stream delivered by the wand 10.

All of the components of wand 10 are of an inexpensive and disposable nature, so that after use they may be discarded.

Operation of disposable surgical site visualization wand 10 of the present invention is relatively simple. The sterile wand 10 and fluid connection assembly 80 are unwrapped in the operating theatre and connected to gas and liquid sources, respectively. With clamps 26 and 26' and roller clamp 90 in their closed positions, male luer connector 88 is connected to luer lock cap 54, a valve to the gas source opened, and clamp 26 released to check for proper gas flow and possible leaks. With clamp 26 open, clamp 26' is also opened, and drip chamber 84 adjusted and roller clamp 90 opened to test for proper flow of liquid into tip 40 from source 82 and creation of a mist of appropriate density. After testing as set forth above, wand 10 is ready for use in surgery. As noted previously, barrel 12 may be bent to the desired angle (See FIG. 3) and fluid flow directed through fan tip or nozzle 40 along a line of contact 100 at the target site 102 in a fan-shaped, substantially planar stream 104 to sweep blood 106 before it and away from the target side 102, where it may be removed with a suction wand. The moisturized, fan-shaped, substantially planar stream 104 permits the operator to brush or sweep the obstructing bodily fluids away from the target site without spattering, and without dehydration necrosis of the patient's tissue. In the event of a confirmed HIV-positive patient, the liquid feed can be increased to produce an extremely heavy mist to help contain patient contaminants within the intracorporeal cavity.

While the present invention has been described in terms of a preferred embodiment, it is not so limited. For example, the liquid reservoir or source may be pressurized and/or liquid delivered into barrel 12 through an atomizer nozzle to enhance the formation of an irrigation mist. Other types of clamps known in the art may be employed with the gas and liquid delivery conduits, and the liquid and gas may be delivered to the wand via a manifold to which both gas and liquid delivery lines are commonly connected. The wand of the present invention might be formed with a manifold defining a pistol-grip and a trigger-actuated variable flow liquid valve for ease of aiming and one-handed control of the wand. These and other additions, deletions and modifications may be made to the preferred embodiment as disclosed without departing from the scope of the invention as hereinafter claimed.

What is claimed is:

1. A wand for delivering a fluid stream having at least a gas component to a target site on a patient, comprising:
    a first conduit defining a tubular barrel having an inlet end for receiving said gas component of said fluid stream from a gas source, and an outlet end;
    a flexible tip at said outlet end of said first conduit and defining a laterally elongated aperture for directing said fluid stream in a planar configuration to said target site; and
    a second conduit having an inlet end exterior to said first conduit for receiving a liquid component of said fluid stream, and an outlet end located beyond said first conduit outlet end and substantially within said tip for delivery of said liquid component into said gas component of said fluid stream.

2. The wand of claim 1, further including gas filter means in communication with said inlet end of said first conduit barrel for filtering microorganism contaminants from said gas component of said fluid stream prior to entry thereof into said barrel.

3. The wand of claim 1 further including valve means for selective occulsion of said second conduit.

4. The wand of claim 3, where said selective occlusion includes partial occlusion.

5. The wand of claim 1, wherein said tip further includes a tapered down portion between said outlet end of said first conduit and said delivery aperture, and said outlet end of said second conduit is disposed proximate said tapered down position.

6. The wand of claim 1, wherein said second conduit extends through the side wall of said first conduit at a location removed from said first conduit outlet end and into said barrel of said first conduit.

7. The wand of claim 1 wherein said laterally elongated delivery aperture of said tip is defined by a fan-shaped nozzle.

* * * * *

UNITED STATES PATENT AND TRADEMARK OFFICE
CERTIFICATE OF CORRECTION

PATENT NO. : 5,336,170

DATED : 8/9/94

INVENTOR(S) : Salerno et al.

It is certified that error appears in the above-indentified patent and that said Letters Patent is hereby corrected as shown below:

In the Abstract, line 4, after "and" change "a" to --an--;

In Column 1, line 14, change "and" to --an--;

In Column 2, line 36, change "vital" to --viral--;

In Column 6, line 9, comma after "1";

In Column 6, line 10, change "occulsion" to --occlusion--;

In Column 6, line 11, change "where" to --wherein--;

In Column 6, line 17, change "position" to --portion--;

In Column 6, line 23, comma after "1".

Signed and Sealed this

Twenty-second Day of November, 1994

Attest:

BRUCE LEHMAN

Attesting Officer

Commissioner of Patents and Trademarks